United States Patent [19]

Gleisner

[11] Patent Number: 5,547,702
[45] Date of Patent: Aug. 20, 1996

[54] METHOD FOR CONTINUOUS MANUFACTURE OF DIAGNOSTIC TEST STRIPS

[75] Inventor: John M. Gleisner, Lynnwood, Wash.

[73] Assignee: Polymer Technology International Corporation, Issaquah, Wash.

[21] Appl. No.: 272,192

[22] Filed: Jul. 8, 1994

[51] Int. Cl.⁶ .......................... G01N 33/531; B05D 3/00; C12Q 1/28; C12Q 1/54
[52] U.S. Cl. .............................. 427/2.13; 435/4; 435/7.1; 435/7.9; 422/56; 422/57
[58] Field of Search .................................. 427/2.13, 285, 427/286, 414, 338; 422/56, 57; 435/4, 7.1, 7.71, 7.9, 7.91

[56] References Cited

U.S. PATENT DOCUMENTS

| | | |
|---|---|---|
| 3,099,605 | 7/1963 | Free et al. . |
| 3,127,281 | 3/1964 | Meyer ..................... 427/2.13 |
| 3,443,903 | 10/1965 | Haack et al. . |
| 3,607,093 | 9/1971 | Stone . |
| 3,715,192 | 2/1973 | Wenz et al. ........................ 23/253 TP |
| 3,980,437 | 9/1976 | Kishimoto et al. . |
| 3,992,158 | 11/1976 | Przybylowicz et al. . |
| 4,042,335 | 8/1977 | Clement . |
| 4,056,468 | 11/1977 | Breiter et al. . |
| 4,166,093 | 8/1979 | Smith-Lewis et al. .................... 422/56 |
| 4,216,245 | 8/1980 | Johnson ................. 427/2.13 |
| 4,281,062 | 7/1981 | Kallis ......................... 435/14 |
| 4,303,753 | 12/1981 | Lam ........................... 435/14 |
| 4,482,583 | 11/1984 | Siddiqu ................... 427/285 |
| 4,562,148 | 12/1985 | Sommer ................... 427/2.13 |
| 4,604,264 | 8/1986 | Rothe et al. ......................... 422/56 |
| 4,837,043 | 6/1989 | Engelmann et al. .................... 427/2.13 |
| 4,874,692 | 10/1989 | Eikenberry ................... 435/7 |
| 4,883,688 | 11/1989 | Houts et al. ........................ 427/285 |
| 4,935,346 | 6/1990 | Philips et al. . |
| 5,047,206 | 9/1991 | Dombrowski ............................ 422/56 |
| 5,059,526 | 10/1991 | Arai et al. ................................. 435/17 |
| 5,128,171 | 7/1992 | Gleisner ................................. 427/2.13 |
| 5,204,061 | 4/1993 | Covington et al. .................... 427/2.13 |
| 5,238,737 | 8/1993 | Burkhardt et al. ....................... 428/328 |
| 5,300,439 | 4/1994 | Charlton ............................... 427/2.11 |

*Primary Examiner*—Diana Dudash
*Attorney, Agent, or Firm*—George W. Neuner

[57] ABSTRACT

A method for making a test strip is described. The test strip is generally a substrate, a layer disposed on the substrate and located near the distal end of the substrate. The layer typically contains a chemical reagent detection system capable of detecting the presence of a predetermined analyte in a sample of biological fluid, wherein the reagent detection system produces a detectable change in the layer in the presence of the analyte. In the method, a length of substrate is provided having a width substantially the dimension of the final length of the test strip being made; on the substrate near one edge thereof is provided a layer of material permeable to biological fluids, the layer having a width sufficient to place thereon a drop of biological fluid for treating; to the layer of permeable material is continuously applied an aqueous solution containing reagent detection chemicals capable of providing a detectable change in the presence of a predetermined analyte, the solution being applied in an amount to substantially saturate the permeable material; the layer of permeable material is dried to contain the reagent detection chemicals within the layer; and the web is cut into predetermined shorter lengths containing a preset number of test strips for further processing.

11 Claims, 1 Drawing Sheet

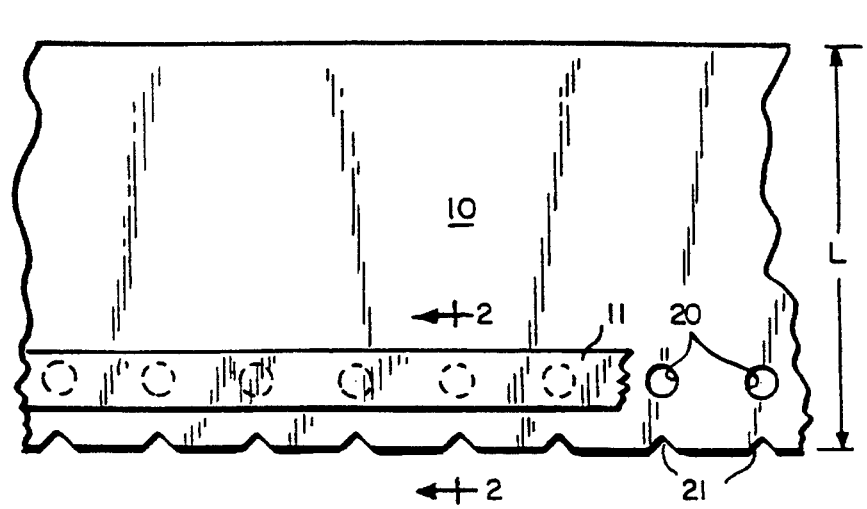
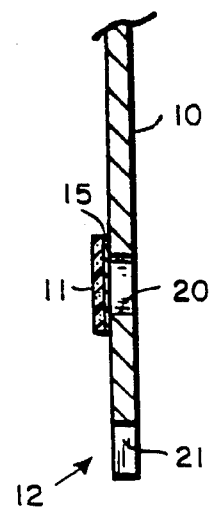
FIG. 1  FIG. 2
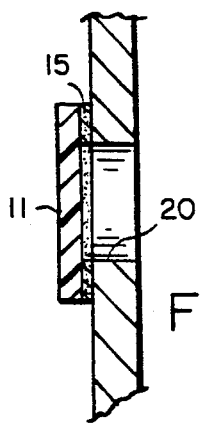
FIG. 2A
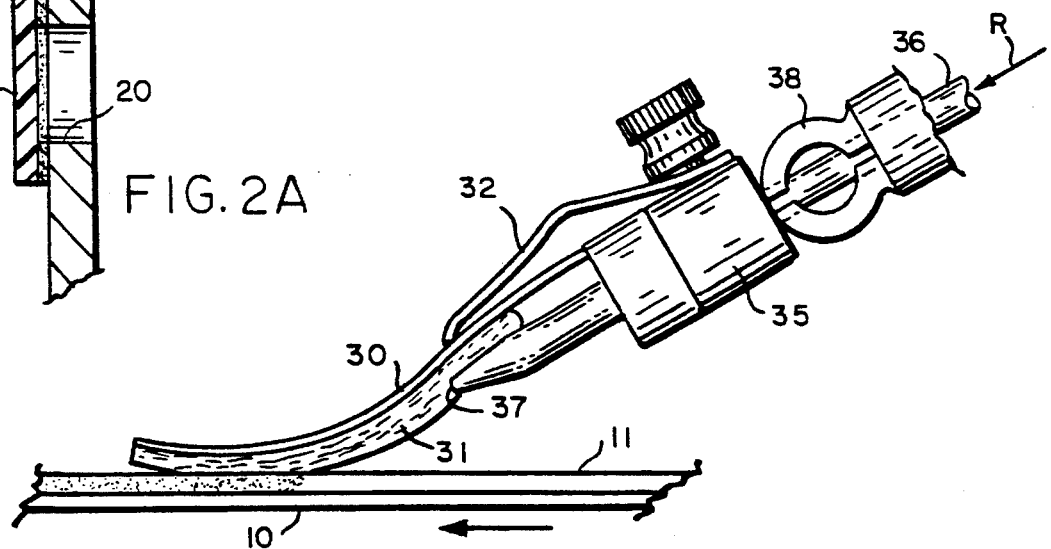
FIG. 3

METHOD FOR CONTINUOUS MANUFACTURE OF DIAGNOSTIC TEST STRIPS

FIELD OF THE INVENTION

This invention is related to diagnostic test strips and, particularly, to improved methods for manufacturing such test strips.

BACKGROUND OF THE INVENTION

Chemical analysis of liquids including water, foodstuffs such as milk, biological fluids, and the like is often desirable or necessary. Dry elements or test strips have been used to facilitate liquid analysis. Such elements have often included a reagent for a substance under analysis, called an analyte. the reagent, upon contact with a liquid sample containing the analyte, causes formation of a colored material or other detectable change in response to the presence and concentration of the analyte in the sample. Various analytical elements using the essentially dry analysis approach have been proposed.

Such "dry" analysis test strips are particularly useful for use in the home for monitoring blood analytes such as glucose. Thus, it is desirable to provide methods for the manufacture of high quality test strips that are economical.

SUMMARY OF THE INVENTION

The present invention provides an improved method for manufacturing diagnostic test strips and the like. The test strips made by the methods of the present invention typically comprise a substrate, a layer disposed on the substrate and located near the distal end of the substrate, said layer containing a chemical reagent detection system capable of detecting the presence of a predetermined analyte in a sample of biological fluid, the reagent detection system producing a detectable change in said layer in the presence of said analyte.

The chemical reagent detection system typically comprises enzymes that react with the predetermined analyte to produce a response in proportion to the amount of analyte present and an indicator that provides a detectable change based on said response produced by the enzymes. Preferably, the detectable change is a visibly detectable change. For producing a visibly detectable change, an indicator such as a dye or dye coupler system is used wherein a change in color is produced proportional to the amount of analyte present in the sample.

In accord with the present invention a method for making test strips comprises: providing a web comprising a length of substrate having a width substantially the dimension of the final length of the test strip being made; placing on said substrate near one edge thereof a layer of material permeable to biological fluids, said layer having a width sufficient to place thereon a drop of biological fluid for treating; continuously applying to the layer of permeable material an aqueous solution containing reagent detection chemicals capable of providing a detectable change in the presence of a predetermined analyte, said solution being applied in an amount to substantially saturate the permeable material; drying the layer of permeable material to contain the reagent detection chemicals within said layer; and cutting the web into predetermined shorter lengths containing a preset number of test strips for further processing.

In one embodiment, the method of the present invention comprises: providing a web comprising a length of substrate having a width substantially the dimension of the final length of the test strip being made; placing on said substrate near one edge thereof a layer of material permeable to biological fluids, said layer having a width sufficient to place thereon a drop of biological fluid for treating; continuously applying to the layer of permeable material a first aqueous solution containing an indicator capable of providing a detectable change in the presence of a predetermined analyte, said first solution being applied in an amount to substantially saturate the permeable material; drying the layer of permeable material to contain the indicator within said layer; continuously applying a second aqueous solution containing enzymes capable of reacting with the predetermined analyte to provide a response that produces a detectable change to the indicator, said second aqueous solution being applied at a rate to provide a predetermined quantity of enzymes in the permeable layer; drying the layer of permeable material to contain the enzymes within said layer; and cutting the web into predetermined shorter lengths containing a preset number of test strips for further processing.

BRIEF DESCRIPTION OF THE DRAWINGS

FIG. 1 is a plan view of a web illustrating a length of substrate having thereon a layer of permeable material in accord with a preferred embodiment of the present invention.

FIG. 2 is an enlarged partial side view, in cross-section, of the web along 2—2 of FIG. 1.

FIG. 2a is a partial view of FIG. 2.

FIG. 3 is a side view illustrating the application of solution to the permeable layer of the web illustrated in FIG. 1 in accord with a preferred embodiment of the invention.

DETAILED DESCRIPTION OF THE INVENTION

Test strips made in accord with the present invention typically comprise a substrate 10 (FIGS. 1 and 2) having a predetermined length "L". The substrate provides support for a layer 11 of material that is permeable to biological fluids and to aqueous solutions. A pad consisting of the layer 11 is disposed at or near the distal end 12 of the substrate 10, when the substrate is cut into individual test strips. The layer of permeable material contains a chemical reagent detection system. In use, the test strip is typically picked up and handled by its proximal end.

As the layer of permeable material, materials useful in the practice of the present invention can include any material having permeability arising from pores or voids, ability to swell, or any other characteristic. Such layers can include a matrix. The choice of a matrix is variable and dependent on the intended use of the element. Useful matrix materials can include hydrophilic materials both naturally occurring such as substances like gelatin, gelatin derivatives, hydrophilic cellulose derivatives, polysaccharides such as dextrin, gum arabic, agarose, and the like, and also synthetic substances such as water-soluble polyvinyl compounds like polyvinyl alcohol, polyvinyl pyrolidone, acrylamide polymers, etc. Organophilic materials such as cellulose esters and the like can also be useful.

The chemical reagent detection system is varied depending on the analyte for which the test strip is designed to test. Typically, the chemical reagents comprise enzymes that react with the analyte to form byproducts and an indicator that reacts with the byproducts to produce a detectable change. Preferably, the detectable change is a visibly detectable change. To produce a visibly detectable change a dye or dye precursor is used as the indicator, as is well known to those skilled in the art.

For example, if one wishes to test for glucose as the analyte in biological fluids such as blood, serum, urine, or the like, etc., typically, a glucose oxidase and a peroxidase are used as enzymes and dye or dye precursor is used as the visibly detectable indicator.

Typical dyes or dye precursors include compositions that, when oxidized, can couple with itself or with its reduced form to provide a dye. Such autocoupling compounds include a variety of hydroxylated compounds such as orthoaminophenols, 4 -alkoxynaphthols, 4-amino-5-pyrazolones, cresols, pyrogallol, guaiacol, orcinol, catechol phloroglucinol, p,p-dihydroxydiphenol, gallic acid, pyrocatechoic acid, salicyclic acid, etc. Compounds of this type are well known and described in the literature, such as in *The Theory of the Photographic Process*, Mees and James, Ed., (1966), especially in Chapter 17.

Other detectable compounds can be provided by oxidation of a leuco dye to provide the corresponding dyestuff form. Representative leuco dyes include such compounds as leucomalachite green, and leucophenolphthalein. Other leuco dyes, called oxichromic compounds, are described in U.S. Pat. No. 3,880,658.

Detectable species can also be provided by dye-providing compositions that include an oxidizable compound capable of undergoing oxidative condensation with couplers such as those containing phenolic groups or activated methylene groups, together with such a coupler. Representative such oxidizable compounds include benzidene and its homologs, p-phenylenediamines, p-aminophenols, 4-aminoantipyrine, etc., and the like. A wide range of such couplers, including a number of autocoupling compounds, is described in the literature, such as Mees and James, supra, and in Kosar, *Light-Sensitive Systems*, 1965, pages 215–249.

Preferred dye couplers include 4-aminoantipyrine (HCl) together with 1,7-dihydroxynaphthalene and 3-dimethylaminobenzoic acid together with 3-methyl-2-benzothiazolinone hydrazone (HCl).

In a preferred embodiment, the substrate for the test strip contains a circular opening 20 located approximately in the center of the area covered by the pad containing the reagent chemistry. Also, a notch 21 may be located in the distal end of substrate, centered with the circular opening.

To make test strips in accord with the present invention a web or length of substrate is provided having a width predetermined by the final length "L" of the test strip to be made. The substrate can be provided in precut lengths of a size that is easily handled or in a large coil.

A strip 11 of a material permeable to biological fluids is disposed on one side of the substrate 10. (FIG. 1) If openings 20 are desired in the substrate, such openings are cut or punched into the substrate prior to adhering the strip 11 thereto. Any suitable adhesive can be used. Conveniently, a two sided adhesive tape 15 can be used to adhere the strip layer 11 to the substrate 10. Preferably, no adhesive is contacted with the portion of the pad that covers the opening 20 in the substrate 10.

The substrate 10 having a strip 11 of permeable material is continuously fed by a suitable conveyor past a coating station for applying the chemical reagents. If the substrate is in precut lengths, the pieces of substrate are placed on the conveyor and butted together for continuous feeding. Alternatively, the substrate can be fed from a large roll of the substrate. At the coating station, a solution of the reagent chemistry is metered onto the permeable material strip to provide a predetermined quantity of chemical reagents in the permeable layer.

The coated layer is then dried at a temperature that is not deleterious to the enzymes. After drying, the substrate is cut into predetermined lengths, each length having a pre-selected number of individual test strips. Appropriate inspections are performed, either before or after cutting. The lengths of substrate are then cut into individual test strips and packaged.

In a preferred embodiment, the reagent chemicals are coated onto the permeable material in two steps. First, the substrate is continuously coated with a solution containing the dye precursor. Preferably, the permeable material is substantially saturated with the solution containing dye precursor by metering the solution onto the permeable material. After drying, the substrate is continuously coated with a metered amount of a second solution containing the enzymes. A second drying step is performed after coating with the enzyme solution.

In one embodiment of the present invention, a glucose test strip is made. First a web of polystyrene, about 0.22 to 0.28 mm thick is provided having a width about 50–65 mm. Near one edge of the web a series of circular openings are provided, the center of the opening being located about 1 cm from the edge, the openings being located about 15 mm apart (center to center), and each opening being about 5 mm in diameter. "V" shaped notches can also be provided at the edge of the substrate, each notch aligned with the center of the corresponding opening. A porous nylon membrane, 8 to 9 nm wide and about 0.10 to 0.20 mm thick is adhered to the polystyrene substrate covering the openings so that the openings are centered on the nylon membrane. Preferably, the nylon membrane is a microporous filter material such as materials sold by Pall, East Hills, N.Y. The adhesive layer is preferably coated on the polystyrene substrate prior to making the openings so that the nylon, membrane will be free of adhesive in the opening of the substrate.

The substrate having the nylon stripe is fed continuously from a roll or is cut into easily handled strips approximately four feet long.

The substrate is fed continuously on a suitable conveyor to a first coating station. In the first coating station, the porous nylon membrane is coated with a solution of dye precursor which is metered to the membrane in an amount that will substantially saturate the membrane. The amount of dye precursor in solution is calculated to provide the amount of dye desired in the test strip in accord with the methods well known to those skilled in the art. The substrate with coated nylon membrane is then fed continuously into a dryer where the solvent is evaporated. The solvent can be a mixture of water and a water miscible organic solvent. Conveniently, the substrate is fed into the coating station at about 25 ft/min and dried under a flow of warm air at about 130° F. for about 15 minutes, or until dry.

After exiting the first dryer, the substrate is continuously fed into a second coating station at about 25 ft/min. At the second station, a solution containing the enzymes, glucose oxidase and horseradish peroxidase, is metered onto the porous nylon membrane so that the membrane will contain a desired quantity of the enzymes to conduct the desired test. Calculation of the enzyme concentrations and metering rate is performed by methods well known to those skilled in the art. After coating, the substrate is again continuously fed into a dryer under a flow of warm air for about 15 minutes.

In one embodiment, each coating station is as illustrated in FIG. 3. The coating station consists of a coating device that consists of a piece of flexible spring steel 30, on which a piece of felt 31 is attached. The spring with attached felt is held in position over the substrate 10 and strip 11 of permeable material by adjustable mounting means (not shown). The spring and attached felt are mounted on a block 35. Attached to the block 35 is another piece of spring steel 32, which is used to apply pressure to spring 30 to keep the felt 31 in contact with the strip layer 11. Coating solution R is fed from a metering pump (not shown) through a tube 36 to the felt 31. The tube end is preferably in the form of a slit 37. A clamp 38 is used to hold the tube in fixed relation to the block 35. The coating solution then travels through the felt to the strip of permeable material in accord with the rate of flow set by the metering pump. An example of a suitable felt for the practice of the present invention is that felt available from the Keystone Franklin Division of National Felt Company.

In a preferred embodiment, the coating station comprises a tube having a slit opening through which the coating solution is metered by a positive displacement pump. After exiting from the slit, the solution is absorbed by an applicator felt, about 8 mm wide, which trails on the porous nylon membrane. The felt applicator is mounted on a stainless steel spring, about 0.005 inch thick. A second stainless steel spring, about 0.032 inch thick, is used to adjust pressure on the felt applicator to provide adequate contact with the porous nylon membrane being coated. Care should be taken to permit the coating solution to flow continuously through the applicator onto the membrane being coated.

After the coating is dried, the coated web is inspected as necessary. After inspection, the web is cut into shorter lengths, each length containing a predetermined number of individual test strips, e.g., twenty-five test strips or fifty test strips. Each shorter length is then cut into the predetermined number of test strips and packaged in suitable containers that are sealed.

The invention has been described in detail including the preferred embodiments thereof. However, it will be appreciated that those skilled in the art, upon consideration of the specification and drawings herein, may make modifications and improvements within the spirit and scope of the present invention.

I claim:

1. A method for making a test strip comprising a substrate, a layer disposed on the substrate and located adjacent the distal end of the substrate, said layer containing a chemical reagent detection system capable of detecting the presence of an analyte in a sample of biological fluid, the reagent detection system producing a detectable change in said layer in the presence of said analyte, said method comprising:

providing a web comprising a length of substrate having a width substantially the dimension of a final length of the test strip being made;

providing on said substrate adjacent to one edge thereof a layer of material permeable to biological fluids, said layer having a width sufficient to place thereon a drop of biological fluid;

continuously applying to the layer of permeable material an aqueous solution containing reagent detection chemicals capable of providing the detectable change in the presence of the analyte, said solution being applied in an amount to substantially saturate the permeable material;

drying the layer of permeable material to contain the reagent detection chemicals within said layer; and cutting the web into shorter lengths of web containing a plurality of test strips for further processing.

2. The method of claim 1 wherein the reagent detection chemicals comprise glucose oxidase, peroxidase and an indicator.

3. The method of claim 2 wherein the indicator is a dye couple consisting of 3-dimethylaminobenzoic acid and 3-methyl-2-benzothiazolinone hydrazone.

4. The method of claim 1, further comprising cutting each shorter length of web into individual test strips and packaging the plurality of test strips in a sealed container.

5. A method for making a test strip comprising a substrate, a layer disposed on the substrate and located adjacent the distal end of the substrate, said layer containing a chemical reagent detection system capable of detecting the presence of an analyte in a sample of biological fluid, the reagent detection system producing a detectable change in said layer in the presence of said analyte, said method comprising:

providing a web comprising a length of substrate having a width substantially the dimension of a final length of the test strip being made;

providing on said substrate adjacent to one edge thereof a layer of material permeable to biological fluids, said layer having a width sufficient to place thereon a drop of biological fluid;

continuously applying to the layer of permeable material a first solution containing an indicator capable of providing the detectable change in the presence of the analyte, said first solution being applied in an amount to substantially saturate the permeable material;

drying the layer of permeable material to contain the indicator within said layer;

continuously applying to the layer of permeable material a second solution comprising an aqueous solution containing enzymes capable of reacting with the analyte to provide a response that produces the detectable change to the indicator, said second solution being applied at a rate to provide a quantity of enzymes in the permeable layer;

drying the layer of permeable material to contain the enzymes within said layer; and cutting the web into shorter lengths of web containing a plurality of test strips for further processing.

6. The method of claim 5 wherein the first solution comprises an indicator dissolved in a mixture of water and a water miscible organic solvent.

7. The method of claim 6 wherein the indicator is a dye couple consisting of 3-dimethylaminobenzoic acid and 3-methyl-2-benzothiazolinone hydrazone.

8. The method of claim 5 wherein the second aqueous solution comprises a solution of glucose oxidase and peroxidase.

9. The method of claim 5 wherein the first solution comprises an indicator dissolved in a mixture of water and a water miscible organic solvent and the second aqueous solution comprises a solution of glucose oxidase and peroxidase.

10. The method of claim 9 wherein the indicator is a dye couple consisting of 3-dimethylaminobenzoic acid and 3-methyl-2-benzothiazolinone hydrazone.

11. The method of claim 5, further comprising cutting each shorter length of web into individual test strips and packaging the plurality of test strips in a sealed container.

* * * * *